(12) United States Patent
Mayer et al.

(10) Patent No.: US 9,506,885 B2
(45) Date of Patent: Nov. 29, 2016

(54) SENSOR CHIP

(71) Applicant: Sensirion AG, Stafa (CH)

(72) Inventors: Felix Mayer, Stafa (CH); Ulrich Bartsch, Meilen (CH); Martin Winger, Meilen (CH); Markus Graf, Zurich (CH); Pascal Gerner, Zurich (CH)

(73) Assignee: Sensirion AG, Stafa (CH)

( * ) Notice: Subject to any disclaimer, the term of this patent is extended or adjusted under 35 U.S.C. 154(b) by 0 days.

(21) Appl. No.: 14/850,031

(22) Filed: Sep. 10, 2015

(65) Prior Publication Data

US 2016/0091446 A1    Mar. 31, 2016

(30) Foreign Application Priority Data

Sep. 26, 2014  (EP) ..................... 14186534

(51) Int. Cl.
| | |
|---|---|
| H01L 27/14 | (2006.01) |
| G01N 27/04 | (2006.01) |
| G01N 27/22 | (2006.01) |
| G01N 27/14 | (2006.01) |
| G01N 33/00 | (2006.01) |

(52) U.S. Cl.
CPC ............ *G01N 27/048* (2013.01); *G01N 27/14* (2013.01); *G01N 27/225* (2013.01); *G01N 33/0036* (2013.01)

(58) Field of Classification Search
CPC ............... G01N 27/048; G01N 27/14; G01N 33/0036; H01L 23/481
USPC ........................................................ 257/414
See application file for complete search history.

(56) References Cited

U.S. PATENT DOCUMENTS

| | | | |
|---|---|---|---|
| 6,528,875 B1 | 3/2003 | Glenn et al. | |
| 6,565,765 B1 | 5/2003 | Weber | |
| 6,840,103 B2 * | 1/2005 | Lee ..................... | H05B 6/6458 338/35 |
| 7,154,372 B2 | 12/2006 | Vanha et al. | |
| 8,736,002 B2 | 5/2014 | Graf et al. | |
| 8,791,532 B2 | 7/2014 | Graf et al. | |
| 2003/0037590 A1 | 2/2003 | Stark | |
| 2003/0179805 A1 | 9/2003 | Hamamoto et al. | |
| 2005/0104204 A1 | 5/2005 | Kawakubo et al. | |
| 2006/0179942 A1 | 8/2006 | Fukaura et al. | |

(Continued)

FOREIGN PATENT DOCUMENTS

| | | |
|---|---|---|
| EP | 0696725 | 2/1996 |
| EP | 2053651 | 4/2009 |

(Continued)

OTHER PUBLICATIONS

Jean Laconte et al., "SOI CMOS Compatible Low-Power Microheater Optimization for the Fabrication of Smart Gas Sensors", IEEE Sensor Journal, vol. 1 No. 5, Oct. 2004, pp. 670-680.

*Primary Examiner* — Tu-Tu Ho
(74) *Attorney, Agent, or Firm* — Cooper & Dunham LLP

(57) ABSTRACT

A sensor chip comprises a substrate (1) with a front side (11) and a back side (12), and an opening (13) in the substrate (1) reaching through from its back side (12) to its front side (11). A stack (2) of dielectric and conducting layers is arranged on the front side (11) of the substrate (1), a portion of which stack (2) spans the opening (13) of the substrate (1). Contact pads (32) are arranged at the front side (11) of the substrate (1) for electrically contacting the sensor chip. A sensing element (4) is arranged on the portion of the stack (2) spanning the opening (13) on a side of the portion facing the opening (13).

20 Claims, 5 Drawing Sheets

(56) References Cited

U.S. PATENT DOCUMENTS

| | | |
|---|---|---|
| 2006/0270108 A1 | 11/2006 | Farnworth et al. |
| 2008/0283991 A1 | 11/2008 | Reinert |
| 2008/0315230 A1 | 12/2008 | Murayama |
| 2009/0065472 A1 | 3/2009 | Asai et al. |
| 2009/0212397 A1 | 8/2009 | Tuttle |
| 2010/0225000 A1 | 9/2010 | Sugizaki et al. |
| 2010/0314700 A1 | 12/2010 | Park et al. |
| 2011/0138882 A1 | 6/2011 | Moon et al. |
| 2014/0091422 A1 | 4/2014 | Barth |
| 2015/0270239 A1 * | 9/2015 | Yang ................ H01L 24/32 257/414 |

FOREIGN PATENT DOCUMENTS

| | | |
|---|---|---|
| EP | 2154713 | 2/2010 |
| EP | 2348292 | 7/2011 |
| EP | 2481703 | 8/2012 |
| EP | 2482310 | 8/2012 |
| EP | 2620768 | 7/2013 |
| EP | 2762865 | 8/2014 |
| WO | 01/56920 | 8/2001 |
| WO | 2005102911 | 11/2005 |
| WO | 2012100360 | 8/2012 |

\* cited by examiner

SENSOR CHIP

CROSS REFERENCE TO RELATED APPLICATION

This application claims priority of European Patent Application 14186534.5, filed Sep. 26, 2014, the contents of which is incorporated herein by reference in its entirety.

TECHNICAL FIELD

The present invention relates to a sensor chip, and a method for manufacturing a sensor chip.

BACKGROUND ART

Subject to the application, sensors tend to be integrated on semiconductor substrates. This kind of manufacturing is beneficial in that the size of the sensors can significantly be reduced compared to discrete type sensors, and such sensors can be arranged together with electronic circuitry integrated on the same semiconductor substrate which circuitry may include functions acting on a signal delivered by the sensor such as amplification, evaluation, etc.

An integrated chip comprising a sensor is called sensor chip in the following. In such sensor chip, the sensor and possibly electronic circuitry are arranged at a front side of a substrate. The circuitry may be formed by CMOS processing, and the building and/or arranging of a sensing element of the sensor on the front side may be implemented in a way compatible to CMOS processing. When such sensor chip needs to be integrated into a processing system, the sensor chip typically will be connected to circuitry residing on a different circuit board, such as a printed circuit board, for example. A preferred way for mounting a sensor chip to such circuit board is a technique called flip chip mounting in which the sensor chip is flipped such that its front side containing the sensing element and the circuitry faces the circuit board and is electrically connected to it. The electrical connection typically is achieved between contact pads arranged at the front side of the sensor chip and contact pads arranged on the circuit board and solder material in between.

However, now the sensing element faces the circuit board which may not be preferred for various reasons: In case the sensor shall detect a quantity of a measure in a medium in the environment of the sensor, such medium may not have sufficient access to the sensing element for the reason of its arrangement facing the circuit board. In addition, and even worse, the sensing element may be affected during handling, and specifically when mounting/soldering the sensor chip to the circuit board, e.g. when applying a solder forming flux.

Disclosure of the Invention

The problem to be solved by the present invention is therefore to provide a sensor chip wherein the sensor element is less exposed during handling the sensor chip.

This problem is solved by a sensor chip according to the features of the independent claim 1, and by a method for manufacturing a sensor chip according to the features of the independent claim 14.

The sensor chip comprises a substrate with a front side and a back side. Contact pads are arranged at the front side of the substrate for electrically contacting the sensor chip. An opening is provided in the substrate reaching through from its back side to its front side. A stack of dielectric and conducting layers is arranged on the front side of the substrate, a portion of which stack spans the opening of the substrate. A sensing element is arranged on the portion of the stack spanning the opening on a side of the portion facing the opening.

A method for manufacturing a sensor chip includes providing a substrate with a front side and a back side, and a stack of dielectric and conducting layers being arranged on the front side of the substrate. An opening is generated in the substrate from its backside for uncovering a portion of the stack. A sensing element is applied on the uncovered portion of the stack through the opening.

The sensor chip can now be mounted to a circuit board with its front side facing the circuit board, i.e. the side where the electronic circuitry if any and the contact chips are arranged at. Such orientation of mounting is also referred to as flip chip mounting. However, the sensing element is not arranged at the front side and as such does not face the circuit board. Hence, the sensing element is sufficiently exposed to the medium to be measured. Nor is the sensing element exposed and endangered during mounting or soldering the sensor chip onto a circuit board. Instead, the sensor element is arranged in a cavity generated by the opening the substrate and the portion of the stack uncovered by the substrate and spanning the opening. Hence, the sensing element is protected from contamination during mounting and soldering the sensor chip to a circuit board.

The substrate advantageously is a semiconductor substrate, and preferably is a silicon substrate. However, the substrate may also be embodied as a ceramic, glass, polymer or other dielectric substrate. In one example, a thickness of the substrate is between 500 µm and 800 µm which is a common standard thicknesses of wafers. In another embodiment, the standard wafer may be thinned and the thickness of the substrate is between 200 µm and 400 µm.

The substrate is provided, and a stack of layers including at least one insulating and/or at least one conducting layer, and preferably consisting of one or more insulating layers and one or more conducting layers, is deposited on one side of the substrate, which is referred to as front side. Preferably, the stack of layers is a stack of CMOS layers defined for applying CMOS manufacturing processes. In such CMOS processing, conductors and other circuitry, and preferably an active electronic circuitry is processed in particular into the substrate, e.g. by doping. The electronic circuitry integrated in the sensor chip may contain e.g. evaluation or amplification circuitry for evaluating or amplifying a signal from the sensing element subject to the application and the scope of functionality of the sensor chip. Preferably, the electronic circuitry is arranged outside a region of the substrate that is reserved for the opening.

This processing may also include defining and manufacturing contact pads in the stack for electrically connecting the sensor chip to the outside world. The contact pads may be processed from a conducting layer of the stack, which may partially be exposed in order to allow contacting. In this example, the contact pads manufactured in the stack serve as contact pads for the sensor chip. In a different embodiment, the stack is covered, in particular without any layer arranged in between, by an insulating layer containing conducting structures referred to as redistribution layer which connects to the contact pads of the stack and provides its own contact pads accessible from the outside. Preferably, the redistribution layer consists of one or more insulating layers and conducting structures. In this context and generally applicable, when an element is arranged at the front side of the substrate, such arrangement shall encompass a deposition of such element onto the front surface of the substrate, but it also shall encompass a deposition of such element onto other layers deposited on the front surface of the substrate such that the element not necessarily touches the substrate itself. Still such elements are arranged at the front side in that they are not arranged at the back side or at lateral sides of the substrate. Of course, the same holds for the back side or any other location.

It is preferred, that electrodes for interacting with the sensing element are arranged on or in the stack, and specifically at the portion of the stack spanning the opening. The stack may contain various conducting layers, one or more of which may be prepared for interaction with the sensing element. Preferably, electrodes are formed in one or more of the conducting layers of the stack, and may either directly contact the sensing element or may contact-free interact with the sensing element, e.g. in a capacitive measurement. Preferably, the stack comprises a bottom dielectric layer facing the opening in the portion of the stack spanning the opening. The electrodes are arranged in or on the bottom dielectric layer in the portion of the stack spanning the opening.

In a way comparable to the building of the electrodes, a heating structure for heating the sensing element may be built in or on the stack. Heating the sensing element may be required for operating the sensing element at an elevated temperature in case of the sensing element comprising metal oxide, for example, which may be applied for implementing a gas sensor. In another embodiment, in case of the sensing element being a temperature sensor or a humidity sensor, heating may be required for provoking a second temperature measurement point in addition to the environmental temperature, e.g. for testing purposes. Preferably, the heating structure is formed in one or more of the conducting layers of the stack. Preferably, the stack comprises a bottom dielectric layer facing the opening in the portion of the stack spanning the opening. The heating structure is arranged in or on the bottom dielectric layer in the portion of the stack spanning the opening. Preferably, the heating structure is manufactured in the same layer as the electrodes are, and preferably by the same manufacturing steps.

The electrodes or the heating structure where applicable may in one embodiment be manufactured during the processing of the electronic circuitry where applicable. Hence, the substrate with the stack deposited thereon but without the opening yet is processed for building the electronic circuitry, the electrodes and/or the heating structure. Afterwards the opening is generated in the substrate from its back side. Specifically, the etching of the opening may reach into parts of the stack and lay open the electrodes or the heating structure respectively.

In a different embodiment, the substrate with the stack deposited thereon may be processed e.g. for integrating electronic circuitry, however, without building the electrodes and/or the heating structure yet. Then, the opening may be generated in the substrate, and the electrodes and/or the heating structure may be manufactured through the opening from the backside of the substrate on or in the portion of the stack facing the opening. This may include an additive deposition of the electrodes and/or the heating structure through the opening in one alternative. In another alternative, this may include structuring the electrodes and/or the heating structure through the opening in one or more layers such as conducting layers of the existing stack. The opening may e.g. be manufactured by etching.

The sensing element, instead, is preferably manufactured through the opening from the back side of the substrate. The material forming the sensing element preferably is applied on the side of the stack facing the opening, or a layer deposited on this side, by contactless dispensing the sensitive material through the opening of the substrate. Contactless dispensing shall include printing, spray coating, and in particular contactless micro-dispensing. In any case the sensing element is applied after the electrodes and/or the heating structure is/are manufactured.

Between the sensing element and any electrodes or heating structure, there may be applied a protective coating for protecting the electrodes and/or the heating structure. Preferably, the protective coating, such as SiN layer, is also applied through the opening from the back side of the substrate, and is deposited prior to the sensitive material, and after having manufactured any electrodes or heating structures if not already been processed before. Then, the sensing element preferably is deposited onto the protective coating.

In an advantageous embodiment, a membrane is arranged at the back side of the substrate and spans the opening distant from the sensing element. Such membrane protects the sensing element while it allows the medium to be measured to access the sensing element. Hence, it is permeable to such medium, e.g. to gas. The membrane preferably is made from a polymer, e.g. from Gore Tex®. The membrane preferably is affixed, e.g. glued, to the substrate or to a layer deposited on the back side of the substrate. The membrane may be provided as a permanent cover in case it allows sufficient access to the sensing element, or, alternatively, as a temporary protection during manufacturing.

The sensor chip may be mounted onto a circuit board as previously discussed without any further packaging. Alternatively, the sensor chip may further be packaged, e.g. by casting a housing, applying a cap wafer on the back side of the substrate, or by other means, and then be mounted onto a circuit board.

In preferred embodiments, the sensor chip is used as one or more of a gas sensor (in particular a humidity sensor), a liquid flow sensor, a gas flow sensor, a pressure sensor, an infrared sensor. Corresponding one or more sensing elements are provided. In a preferred embodiment, two or more sensing elements are provided which may be sensitive to different measurands. Specifically, the sensing elements are differently sensitive to at least two measurands, one of which measurands can be humidity (i.e. gaseous water in a gaseous carrier). For example, one sensing element can be primarily sensitive to humidity only, while the other shows a strong sensitivity to a gas other than water. Hence, by combining measurements from the two sensors, a quantitative or qualitative analysis of humidity as well as of said other gas can be achieved. In one embodiment, these multiple sensing elements are provided on the same portion of the stack and therefore are applied through the common opening. In a different embodiment, for each sensing element a different opening is manufactured into the substrate, and each sensing element is applied to a different portion of the stack, each portion spanning a different opening. The various openings may be manufactured in the same step, e.g. by etching. In any such scenario of more than one sensing element, it is preferred, that each sensing element is manufactured through its assigned opening by a similar or the same manufacturing step, e.g. by contactless dispensing the subject sensitive material through the respective opening of the substrate. The subject sensitive material may be dispensed through the various openings simultaneously, or sequentially. A print head may be provided with different chambers containing the different sensitive materials. Separate openings are advantageous in that the various sensing elements can thermally be controlled independent from each other. In addition, for each sensing element, a deposition space is defined by the walls of the opening without any further means.

Preferably, multiple sensor chips are manufactured from a common wafer. In particular, it can be envisaged that all the steps previously discussed are processed on the wafer while the wafer is diced into the individual sensor chips after these steps. Hence, it is preferred that openings for multiple sensing elements are generated in the wafer from its backside, and preferably generated simultaneously. It is preferred that a sensing element is applied in each opening of the wafer before dicing the wafer, either simultaneously, or in sequence.

Alternatively, some steps can occur after dicing the wafer. For example, the sensing elements can be applied after dicing, i.e. for the sensor chips individually.

Advantageous embodiments of the present idea are listed in the dependent claims as well as in the description below.

All the described embodiments shall similarly pertain to the sensor chip, its use, and to the method for manufatcuring a sensor chip. Synergetic effects may arise from different combinations of the embodiments although they might not be described in detail. Further on it shall be noted that all embodiments of the present invention concerning a method might be carried out in the order of the steps as described or in any other order unless otherwise explicitly mentioned. The disclosure and scope of the invention shall include any order of steps irrespective of the order listed in the claims.

BRIEF DESCRIPTION OF THE DRAWINGS

The embodiments defined above and further embodiments, features and advantages of the present invention can also be derived from the examples of embodiments to be described hereinafter in connection with the drawings in which the figures illustrate.

MODES FOR CARRYING OUT THE INVENTION

Figure 1:
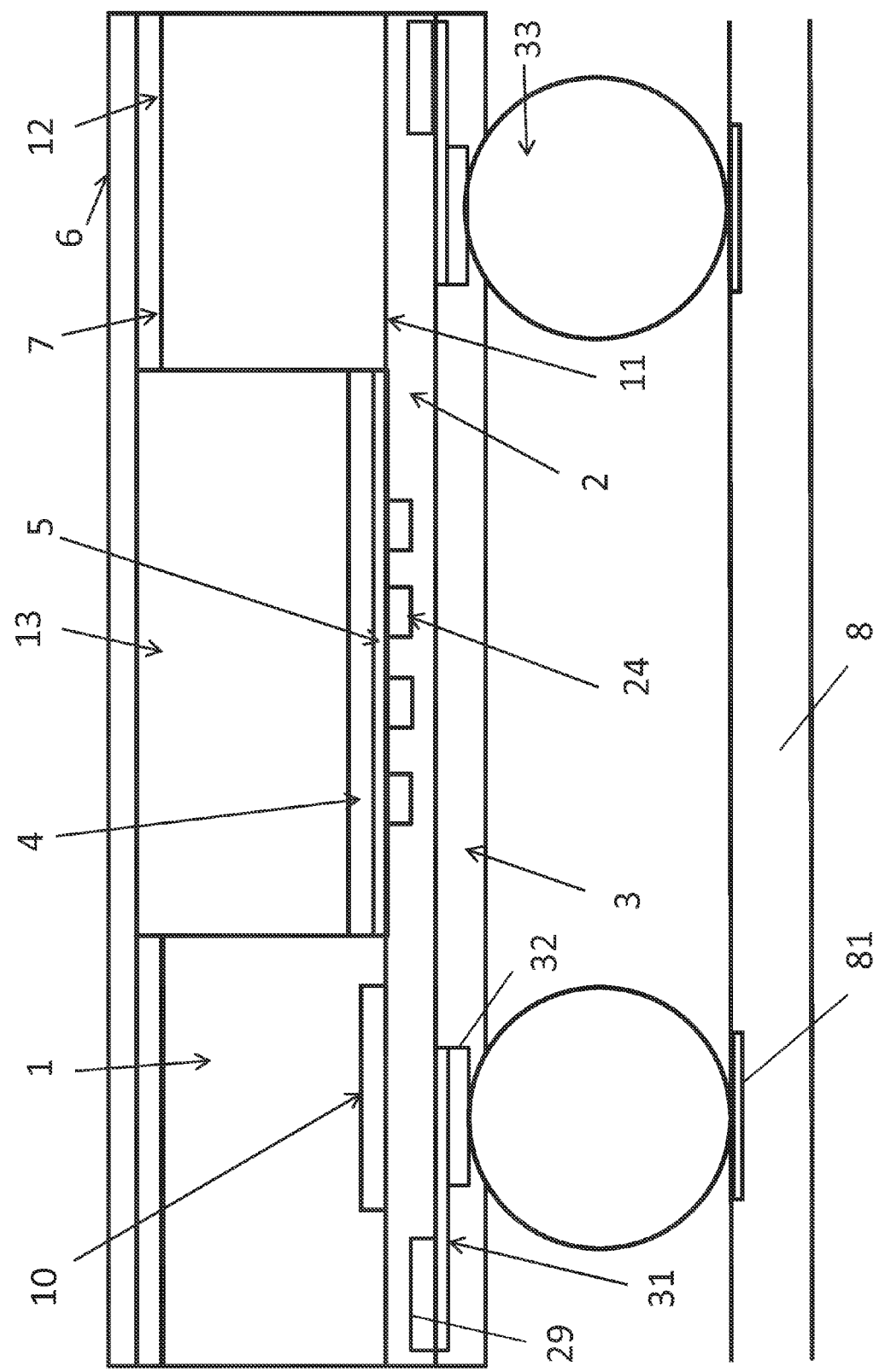
FIG. 1 a sensor chip according to an embodiment of the present invention, in a cross-section, FIG. 2 a sensor chip according to another embodiment of the present invention, in across-section, FIG. 3 a sensor chip according to a further embodiment of the present invention, in a cross-section, FIG. 4 a section of the stacks of a sensor chip according to another embodiment of the present invention in three variants, in a cross-section each, and FIG. 5 a flowchart of a method according to another embodiment of the present invention.

According to FIG. 1, a sensor chip is shown according to an embodiment of the present invention.

The sensor chip comprises a substrate 1 with a front side 11 and a back side 12. The substrate 1 comprises an opening 13 through the substrate 1 from its back side 12 to its front side 11, which opening 13 in one embodiment is arranged in the middle of the sensor chip. In one embodiment, the opening 13 of the substrate may have a diameter between 100 μm and 500 μm.

A stack of dielectric and conducting layers is arranged on the front side 11 of the substrate 1 and is collectively referred to by 2. The dielectric layer(s) of this stack 2 may contain SiO or SiN, the metal conducting layer(s) may contain metal, such as Al, or polysilicon. The stack 2 spans the opening 13 and contributes to a membrane like structure which represents a thermally insulated region of the sensor chip. Generally, and independent from the present embodiment, it is preferred that the membrane like structure completely covers the opening 13 and hence separates the opening 13 from the front side 11 of the substrate 1. However, in a different embodiment, the membrane like structure does not cover the opening completely and, instead, may comprise one or more perforations.

The layers of the stack 2 are preferably CMOS layers and may inter alia be used for contacting an electronic circuit 10 integrated into the substrate 1. One of or more of the conducting layers may also be used for building contact pads 29 for contacting the sensor chip from the outside. In addition, another one or more of the conducting layers may be used for building electrodes 24. The electrodes are preferably built in or on the portion of the stack spanning the opening 13.

On the portion of the stack 2 spanning the opening 13, a sensing element 4 is arranged. In the present example, the sensing element 4 can be separated from the electrodes 24 in the stack 2 by means of a protection layer 5 because no direct ohmic contact between the electrodes 24 and the sensing element 4 is required. Hence, on a side of the stack 2 in the portion facing the opening 13, first a protective coating 5 and then the sensing element 4 are applied.

The sensing element 4 may comprise a sensing layer containing a material that is sensitive to the measure desired to be measured. In one example, the sensing element 4 is sensitive to humidity and the sensor chip may be a humidity sensor. In this example, the electrodes 24 as shown may only constitute a portion of a larger electrode formation such as interdigitated electrodes, which may interact with the sensing element 4. Preferably, the electrodes 24 measure a capacity of the sensing element 4 which sensing element 4 in one embodiment is a polymer.

Even though it has been mentioned that the electrodes can be interdigitated electrodes, different electrode designs, such as a simple pair of electrodes, can be used as well.

In another embodiment, the sensing element 4 may comprise a sensing layer that is sensitive to one or more analytes other than humidity. Here, the sensor chip may be a gas sensor sensitive to at least one gas component other than water. In this example, the electrodes 24 may interact with the sensing element 4 by way of ohmic, i.e. resistive, contact for enabling a measurement of a resistance of the sensing element 4. In this case, protection layer 5 is omitted at least in the region of the electrodes 24. The sensing element 4 in one embodiment contains a metal oxide (MOX) material.

Optionally, another insulating layer 3 may be arranged on the stack 2 such as shown in FIG. 1. The insulating layer 3 comprises a conducting redistribution layer 31 and contact pads 32 of the sensor chip, which are exposed from the insulating layer 3.

Attached to the contact pads 32 are conducting elements 33, which in the present example are solder balls. They may, however, also be other types of conducting elements arranged on the contact pads 32 and protruding over the front face of the substrate 1.

In the present example, the sensor chip is arranged on a conductor board 8, which may, for example, be a printed circuit board. The conductor board 8 comprises contact pads 81, which are connected via the solder balls to the contact pads 32 of the sensor chip. The arrangement of the sensor chip on the conductor board is collectively referred to as sensor device.

At the back side 12 of the substrate, there is provided an optional optically opaque layer 7 which may or may not span the opening 13. This optically opaque layer 7 provides optical protection especially for the electronic circuitry 10, and may be made from metal, for example. Optical opaqueness may also include ultraviolet opaqueness, visible opaqueness and/or infrared opaqueness as desired.

In addition, there may be an optional membrane 6 arranged on the back side of the substrate 1, and in this embodiment on top of the optical protective layer 6, however, which membrane 6 also spans the opening 13 given that it shall serve as a mechanical protection for the sensing element 4. The membrane preferably is permeable to the medium to be measured.

If the optically opaque layer 7 does span the opening 13, it should be permeable, just as the membrane 6. In fact, membrane 6 and optically opaque layer 7 are advantageously formed by the same layer of material.

Figure 2:
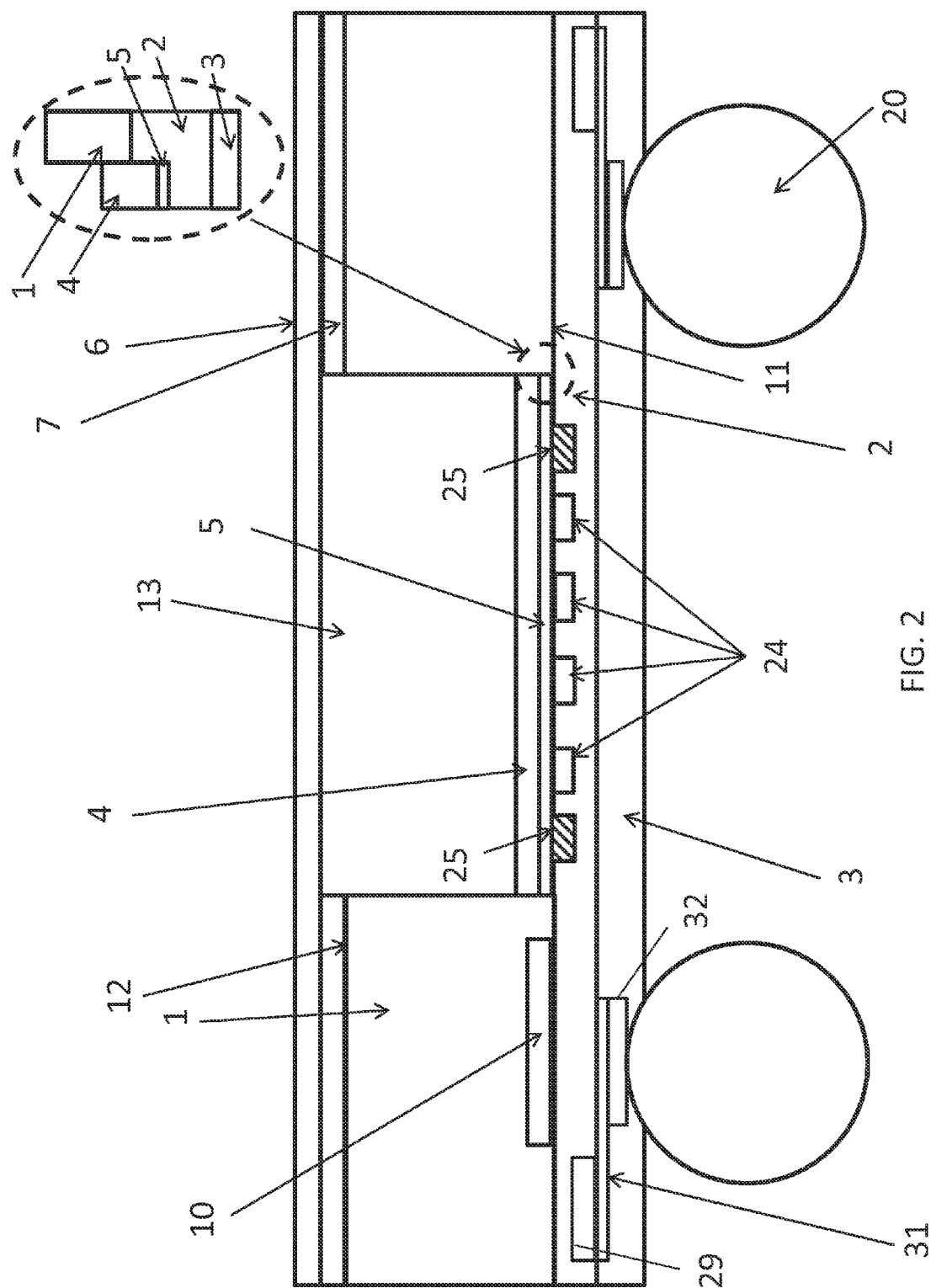

According to FIG. 2 a sensor chip is presented according to another embodiment of the present invention, again in across-section. Identical elements are referred to by the same reference numerals as in FIG. 1.

This embodiment differs from the embodiment of FIG. 1 in that in addition to the electrodes 24 arranged on or in the stack 2 of layers, a heating structure 25 is arranged thereon or therein. The heating structure 25 may be a resistive heating structure and serves for heating the sensing element 4.

A second difference compared to the embodiment of FIG. 1 is shown in more detail in the enlarged section. Here, it becomes apparent that the opening 13 generated in the substrate 1 reaches through the entire depth of the substrate 1 and even to some extent into the stack 2. By this means, the portion of the stack 2 spanning the opening 13 is further thinned, i.e. reduced in thickness. Hence, the sensing element 4 and, if applicable, the protective coating 5 are arranged at a lower level compared to FIG. 1.

Figure 3:
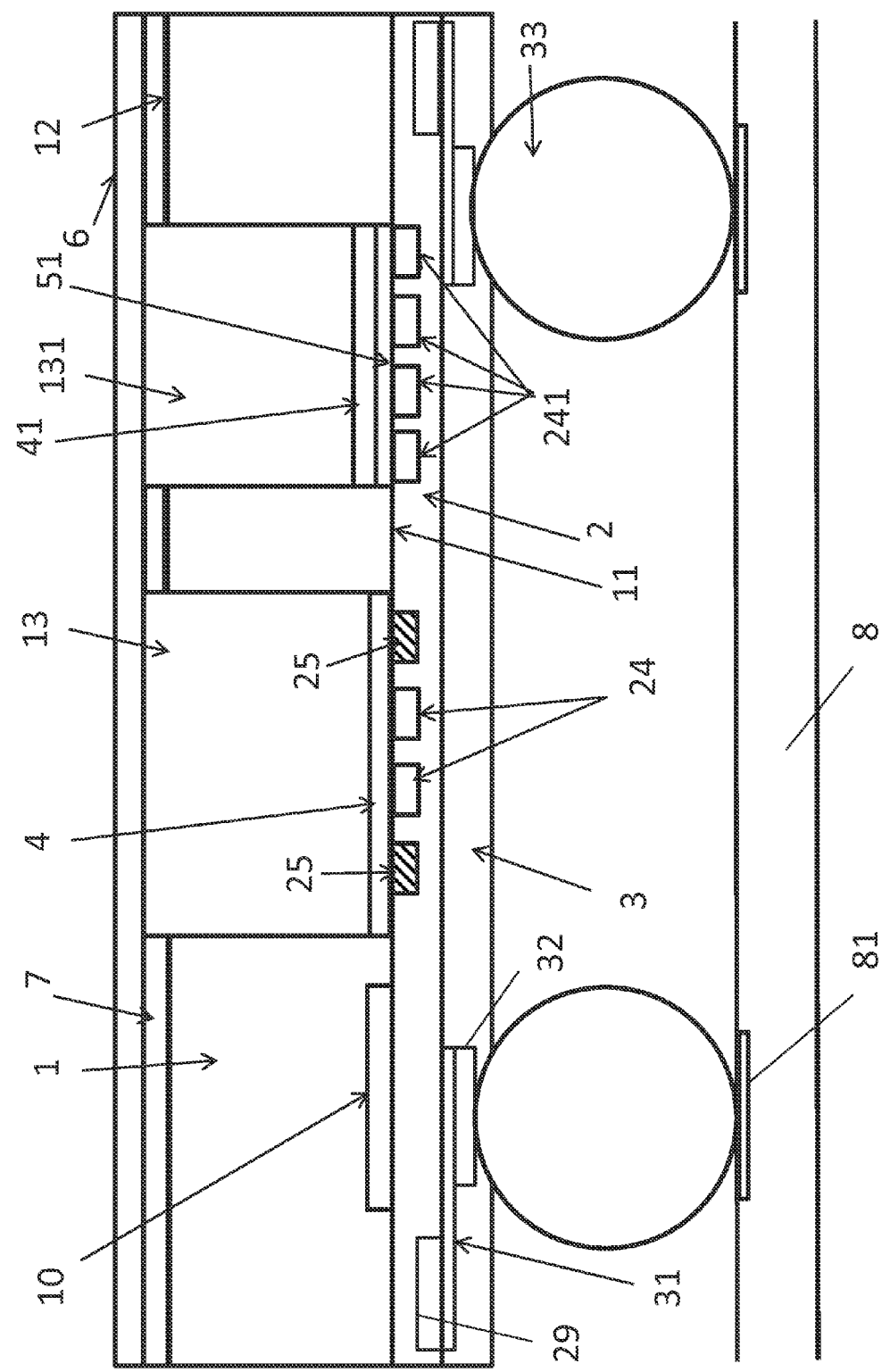

According to FIG. 3 a sensor chip is presented according to a further embodiment of the present invention, again in a cross-sectional view. In this embodiment, two sensing elements 4 and 41 are provided, wherein it is specifically assumed, that the sensing element 41, which can e.g. be a polymer layer, is primarily sensitive to humidity and its corresponding electrodes 241 are interdigitated for conducting a capacitive measurement. In contrast to this, the sensing element 4 is sensitive to at least one gaseous analyte other than water and may specifically contain a metal oxide that will become receptive to the analyte under the application of heat, which will be provided by a heating structure 25. Electrodes 24 may measure a resistance of the sensing element 4. In the present example, each sensing element 4, 41 is applied through a dedicated opening 13, 131. The openings 13 and 131 may lie next to each other, such as depicted, and may be separated by a wall of the substrate 1. In another embodiment, one of the openings may encircle the other opening in form of a ring structure.

Figure 4:
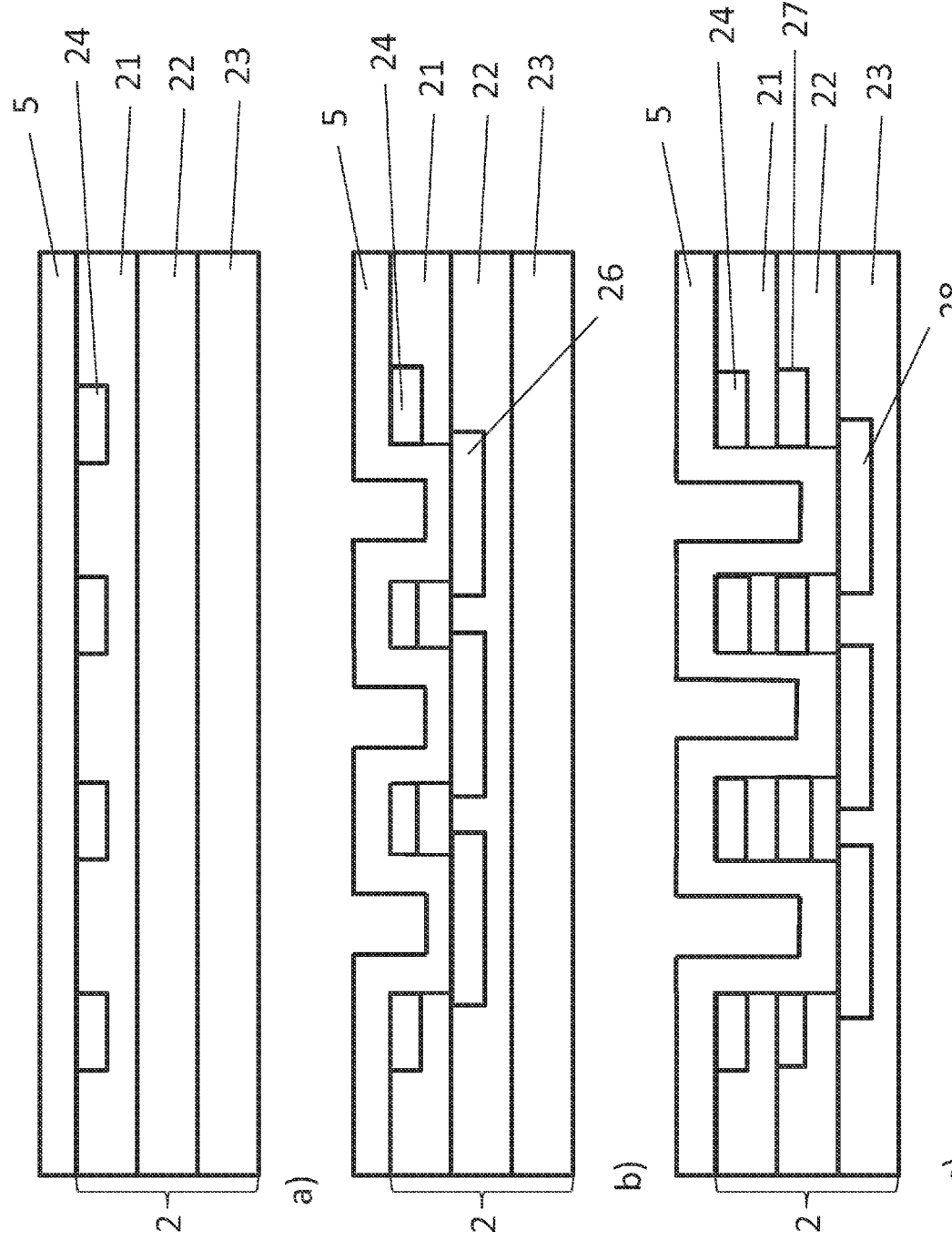

FIG. 4 illustrates various embodiments of stacks 2 of a sensor chip according to embodiments of the present invention. For all variants, it may be assumed that the stack 2 at least comprises three layers of insulating material referred to by 21 to 23. Between each of these layers a conducting layer is provided which is structured and replenished with insulating material such that the present stacks 2 evolve. In FIG. 4a), the conducting layers between the insulating layers 21 and 22 and between 22 and 23 may either be completely removed, or still be present but not illustrated, or may be structured for other purposes. It is only in the first conducting layer where electrodes 24 are provided for interacting with a sensing element later on to be arranged on the stack 2. In the present case, the electrodes are interdigitad electrodes.

The first conducting layer from which the electrodes are built is also referred to as M1 layer in the context of CMOS processing. On top of the electrodes 24, a protective coating 5 is deposited, on which finally the sensitive material will be deposited for building the sensing element. There may be other insulating and conducting layers than the ones shown. E.g., below insulating layer 23, there may be more conducting layers and insulating layers.

In diagram 4b), again the electrodes are formed in the first conducting layer M1. These electrodes 24 are formed by etching and thereby using etch stop structures 26 in the second conducting layer M2 for terminating the etching around the electrodes in the first conducting layer M1. The etching may be pre-processed prior to etching the opening in the substrate 1, or may be processed through the opening 13 after its generation. The resulting structure is then coated optionally by the protective coating 5.

In diagram 4c), electrodes 24 and 27 are formed in two different conducting layers, such as M1 and M2, by etching and thereby using etch stop structures 28 in the third conducting layer M3 for terminating the etching. The resulting structure is then optionally coated by the protective coating 5. The etching may be pre-processed prior to etching the opening in the substrate 1, or may be processed through the opening 13 after its generation.

Figure 5:
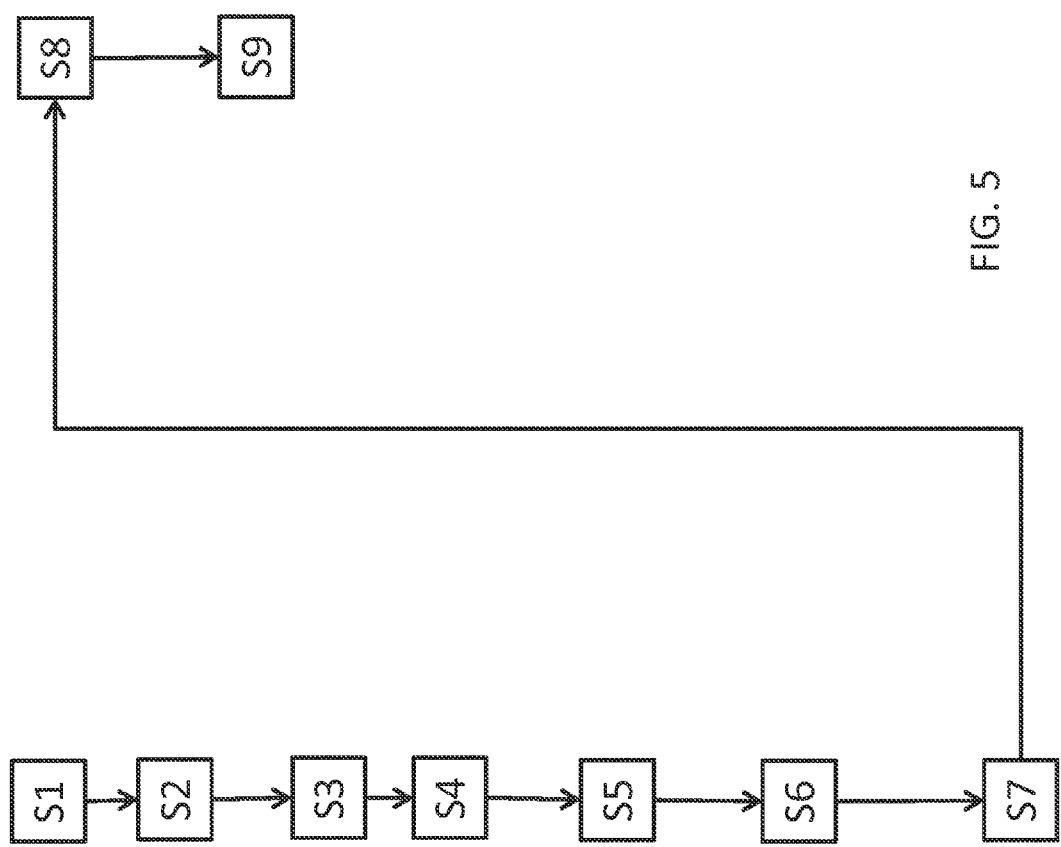

FIG. 5 illustrates a flowchart of a method according to an embodiment of the present invention.

In the present embodiment, in step S1 a substrate with a stack of layers arranged on a front side thereof is provided. Preferably, the stack is a stack of CMOS layers. It is assumed that at this stage, an electronic circuit is already integrated into the substrate, and that the layers of the stack are structure such that the electronic circuit is contacted the way desired. In addition, it is assumed that any electrodes and/or heating structures that are meant to later on interact with the sensing element to be applied, are already structured in the stack preferably from one or more of the conducting layers comprised in the stack of CMOS layers.

In a next step S2, which is optional subject to the need for an intermediate redistribution layer, an insulating layer and metal paths therein may be manufactured on top of the stack at the front side of the substrate, for mapping contact pads exposed from the stack of CMOS layers into contact pads at a different location, a different distance, or of a different size, which contact pads are accessible from the outside for electrically contacting the sensor chip via the contacting elements (solder balls).

In step S3, an opening is etched from the backside of the substrate. Here, the substrate preferably is etched through from its back side to its front side, stopping at the stack of layers, or slightly etching there into.

In case electrodes are not formed yet, they are formed now in step S4 though the opening on the side of the portion of the substrate facing the opening. Etching and cleaning steps may be involved. This step may also include the etching of insulating material from the stack in order to expose and/or contact already formed electrodes.

In subsequent optional step S5, a protective coating is applied through the opening onto the side of the stack that faces the opening.

In step S6, a sensing element is applied through the opening onto the side of the stack that faces the opening. In case a protective coating is applied in step S4, the sensing element is deposited onto the protective coating.

In optional step S7, the optically opaque layer and the protective membrane are applied thereto, advantageously as a single layer of material fulfilling both functions, or separately. This layer or these layers can e.g. by glued to the substrate. The protective membrane spans the opening in the substrate.

In step S8, the conducting elements 33, such as solder balls, are deposited on contact pads at the front side of the substrate. In case there is provided a redistribution layer according to step S2, the solder balls may be deposited on contact pads formed therein/on. In case step S2 was omitted, the solder balls may directly be deposited onto the contact pads built in the stack from one or more conducting layers.

In case multiple sensor chip are manufactured from a wafer, at least some or all of the steps S1 to S8 can be provided on wafer scale, i.e. prior to separating the wafer into individual sensor chips. For example, multiple openings are etched into the wafer, either simultaneously or sequentially.

In step S9, the wafer may be separated e.g. by dicing, into multiple individual sensor chips.

As mentioned, steps S1 to S9 do not have to be executed in the order of FIG. 5, unless noted differently. For example, steps S7 and S8 may also be swapped, or step S6 can be carried out after dicing (i.e. after step S9).

The invention claimed is:
1. A sensor chip, comprising
a substrate with a front side and a back side,
an opening in the substrate reaching through from its back side to its front side,
a stack of dielectric and conducting layers arranged on the front side of the substrate, a portion of which stack spans the opening in the substrate,
contact pads arranged at the front side of the substrate for electrically contacting the sensor chip, and
a sensing element arranged on the portion of the stack spanning the opening on a side of the portion facing the opening,
wherein electronic circuitry is integrated into the sensor chip at the front side of the substrate.
2. A sensor chip according to claim 1 further comprising contacting elements arranged at said contact pads and protruding over a front surface of said substrate.
3. A sensor chip according to claim 1, comprising
electrodes for interacting with the sensing element, which electrodes are arranged on or in the portion of the stack spanning the opening,
wherein the stack comprises a bottom dielectric layer facing the opening in the portion of the stack spanning the opening, and
wherein the electrodes are arranged in or on the bottom dielectric layer of the stack.
4. A sensor chip according to claim 1, comprising
a heating structure for heating the sensing element, which heating structure is arranged on or in the portion of the stack spanning the opening.
5. A sensor chip according to claim 4,
wherein the stack comprises a bottom dielectric layer facing the opening in the portion of the stack spanning the opening, and wherein the heating structure is arranged in or on the bottom dielectric layer of the stack.
6. A sensor chip according to claim 1, comprising
the contact pads being processed from a conducting layer of the stack which conducting layer is partially exposed in order to allow contacting, or
the stack being covered by a redistribution layer comprising an insulating layer containing conducting structures, which redistribution layer connects to the contact pads of the stack and provides its own contact pads accessible from the outside.
7. A sensor chip according to claim 6, comprising
the stack of dielectric and conducting layers being a stack of CMOS layers defined for applying CMOS manufacturing processes.
8. A sensor chip according to claim 1, comprising
a membrane arranged at the backside of the substrate and spanning the opening, which membrane is permeable for a medium to be measured.
9. A sensor chip according to claim 1,
wherein the sensing element is sensitive to at least one measurand, and
a) wherein said at least one measurand comprises humidity or
b) wherein said at least one measurand comprises a substance other than humidity.
10. Sensor A sensor chip according to claim 1, comprising
another opening in the substrate reaching through from its back side to its front side,
another portion of the stack spanning the other opening in the substrate, and
another sensing element arranged on the other portion of the stack spanning the other opening on a side of the other portion facing the other opening.
11. A sensor module, comprising
a circuit board comprising contact pads, and
a sensor chip according to claim 1 arranged on the circuit board with the stack facing the circuit board and the sensing element facing away from the circuit board, and
wherein the contact pads of the sensor chip are electrically connected to the contact pads of the circuit board.
12. A sensor chip, comprising
a substrate with a front side and a back side,
an opening in the substrate reaching through from its back side to its front side,
a stack of dielectric and conducting layers arranged on the front side of the substrate, a portion of which stack spans the opening in the substrate,
contact pads arranged at the front side of the substrate for electrically contacting the sensor chip,
a sensing element arranged on the portion of the stack spanning the opening on a side of the portion facing the opening, and
a heating structure for heating the sensing element, which heating structure is arranged on or in the portion of the stack spanning the opening
wherein electronic circuitry is integrated into the sensor chip at the front side of the substrate.
13. A method for manufacturing a sensor chip, comprising the steps of
providing a substrate with a front side and a back side, and a stack of dielectric and conducting layers arranged on the front side of the substrate,
generating an opening in the substrate from its backside for uncovering a portion of the stack, and
applying a sensing element on the uncovered portion of the stack through the opening.
14. A method according to claim 13,
wherein the sensing element is applied by contactless dispensing sensitive material through the opening of the substrate from its backside.

15. A method according to claim 13,
wherein the opening in the substrate is generated by etching the substrate from its backside.

16. A method according to claim 13,
wherein prior to applying the sensing element through the opening, electrodes for interacting with the sensing element are manufactured through the opening on or in the uncovered portion of the stack.

17. A method according to claim 16,
wherein prior to applying the sensing element and after having manufactured the electrodes, a protective coating is applied on top of the electrodes, and wherein the sensing element is applied onto the protective coating.

18. A method according to claim 13,
wherein prior to applying the sensing element through the opening, a heating structure for heating the sensing element is manufactured through the opening on or in the uncovered portion of the stack.

19. A method according to claim 18,
wherein prior to applying the sensing element and after having manufactured the heating structure, a protective coating is applied on top of the heating structure, and
wherein the sensing element is applied onto the protective coating.

20. A method according to claim 13,
wherein the substrate is provided in form of a wafer for building multiple sensor chips from,
wherein openings for multiple sensing elements are generated in the wafer from its backside,
wherein a sensing element is applied in each opening of the wafer, and
wherein the wafer is diced into the multiple sensor chips after having applied the sensing elements.

* * * * *